United States Patent
Desai et al.

(10) Patent No.: US 7,297,715 B2
(45) Date of Patent: Nov. 20, 2007

(54) PPAR ALPHA SELECTIVE COMPOUNDS FOR THE TREATMENT OF DYSLIPIDEMIA AND OTHER LIPID DISORDERS

(75) Inventors: Ranjit C. Desai, Kendall PK, NJ (US); Soumya Sahoo, Old Bridge, NJ (US)

(73) Assignee: Merck & Co., Inc., Rahway, NJ (US)

( * ) Notice: Subject to any disclaimer, the term of this patent is extended or adjusted under 35 U.S.C. 154(b) by 76 days.

(21) Appl. No.: 10/522,646

(22) PCT Filed: Jul. 25, 2003

(86) PCT No.: PCT/US03/23499

§ 371 (c)(1),
(2), (4) Date: Sep. 26, 2005

(87) PCT Pub. No.: WO2004/010992

PCT Pub. Date: Feb. 5, 2004

(65) Prior Publication Data

US 2006/0089404 A1  Apr. 27, 2006

Related U.S. Application Data

(60) Provisional application No. 60/399,518, filed on Jul. 30, 2002.

(51) Int. Cl.
*A61K 31/352* (2006.01)
*C07D 311/04* (2006.01)

(52) U.S. Cl. .............. 514/456; 549/408; 549/407; 549/398

(58) Field of Classification Search .......... 514/456; 549/408, 407, 398
See application file for complete search history.

(56) References Cited

U.S. PATENT DOCUMENTS 4,565,882 A  1/1986 Miyano et al.

FOREIGN PATENT DOCUMENTS

WO  WO 02/26729  4/2002

OTHER PUBLICATIONS

Abbott Laboratories, "Tricor® 48 mg and 145 mg (fenofibrate tablets)", Prescribing Information, 1994.

*Primary Examiner*—Charanjit S. Aulakh
(74) *Attorney, Agent, or Firm*—James L. McGinnis; Mark Daniel

(57) ABSTRACT

A class of chromane and chromene compounds having the structure shown below and pharmaceutically acceptable salts thereof are useful as therapeutic compounds, particularly in the treatment and control of hyperlipidemia, hypercholesterolemia, dyslipidemia, and other lipid disorders, and in delaying the onset of or reducing the risk of conditions and sequelae that are associated with these diseases, such as atherosclerosis

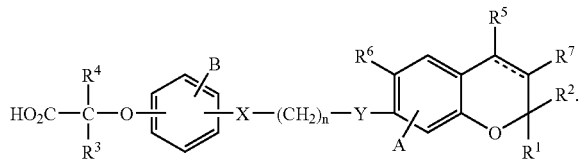

15 Claims, No Drawings

PPAR ALPHA SELECTIVE COMPOUNDS FOR THE TREATMENT OF DYSLIPIDEMIA AND OTHER LIPID DISORDERS

CROSS REFERENCE TO RELATED APPLICATIONS

This application is a U.S. National Phase application under 35 U.S.C. § 371 of PCT Application No. PCT/US03/23499, filed Jul. 25, 2003, and claims priority under 35 U.S.C. § 119 (e) from U.S. patent application Ser. No. 60/399,518 filed Jul. 30, 2002.

FIELD OF THE INVENTION

The instant invention is concerned with a class of chromane and chromene compounds and pharmaceutically acceptable salts thereof which are useful as therapeutic compounds, particularly in the treatment and control of hyperlipidemia, hypercholesterolemia, dyslipidemia, and other lipid disorders, and in delaying the onset of or reducing the risk of conditions and sequelae that are associated with these diseases, including atherosclerosis and Type 2 diabetes mellitus, often referred to as non-insulin dependent diabetes (NIDDM).

BACKGROUND OF THE INVENTION

Disorders of lipid metabolism (dyslipidemias) include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as Low Density Lipoproteins (LDL), Very Low Density Lipoproteins (VLDL) and Intermediate Density Lipoproteins (IDL)). Cholesterol is mostly carried in Low Density Lipoproteins (LDL), and this component is commonly known as the "bad" cholesterol because it has been shown that elevations in LDL-cholesterol correlate closely to the risk of coronary heart disease. A smaller component of cholesterol is carried in the High Density Lipoproteins (HDL) and is commonly known as the "good" cholesterol. In fact, it is known that the primary function of HDL is to accept cholesterol deposited in the arterial wall and to transport it back to the liver for disposal through the intestine. Although it is desirable to lower elevated levels of LDL cholesterol, it is also desirable to increase levels of HDL cholesterol. Generally, it has been found that increased levels of HDL are associated with lower risk for coronary heart disease (CHD). See, for example, Gordon, et al., Am. J. Med., 62, 707-714 (1977); Stampfer, et al., N. England J. Med., 325, 373-381 (1991); and Kannel, et al., Ann. Internal Med., 90, 85-91 (1979). An example of an HDL raising agent is nicotinic acid, a drug with limited utility because doses that achieve HDL raising are associated with undesirable effects, such as flushing.

Dyslipidemias were originally classified by Fredrickson according to the combination of alterations mentioned above. The Fredrickson classification includes 6 phenotypes (i.e., I, IIa, IIb, III, IV and V) with the most common being the isolated hypercholesterolemia (or type IIa) which is usually accompanied by elevated concentrations of total and LDL cholesterol. The initial treatment for hypercholesterolemia is often to modify the diet to one low in fat and cholesterol, coupled with appropriate physical exercise, followed by drug therapy when LDL-lowering goals are not met by diet and exercise alone A second common form of dyslipidemia is the mixed or combined hyperlipidemia or type IIb and III of the Fredrickson classification. This dyslipidemia is often prevalent in patients with type 2 diabetes, obesity and the metabolic syndrome. In this dyslipidemia there are modest elevations of LDL-cholesterol, accompanied by more pronounced elevations of small dense LDL-cholesterol particles, VLDL and/or IDL (i.e., triglyceride rich lipoproteins), and total triglycerides. In addition, concentrations of HDL are often low.

Peroxisome proliferators are a structurally diverse group of compounds that when administered to rodents elicit dramatic increases in the size and number of hepatic and renal peroxisomes, as well as concomitant increases in the capacity of peroxisomes to metabolize fatty acids via increased expression of the enzymes of the beta-oxidation cycle. Compounds of this group include but are not limited to the fibrate class of lipid modulating drugs, herbicides, phthalate plasticizers and the glitazones, a class of compounds that has been under investigation for the treatment of type 2 diabetes. Peroxisome proliferation is also triggered by dietary or physiological factors such as a high-fat diet and cold acclimatization.

Three sub-types of peroxisome proliferator activated receptor (PPAR) have been discovered and described; they are peroxisome proliferator activated receptor alpha (PPARα), peroxisome proliferator activated receptor gamma (PPARγ) and peroxisome proliferator activated receptor delta (PPARδ). PPARα is activated by a number of medium and long-chain fatty acids, and it is involved in stimulating β-oxidation of fatty acids. PPARα is also associated with the activity of fibrates and fatty acids in rodents and humans. Fibric acid derivatives such as clofibrate, fenofibrate, bezafibrate, ciprofibrate, beclofibrate and etofibrate, as well as gemfibrozil, each of which are PPARα ligands and/or activators, produce a substantial reduction in plasma triglycerides as well as some increase in HDL. The effects on LDL cholesterol are inconsistent and might depend upon the compound and/or the dyslipidemic phenotype. For these reasons, this class of compounds has been primarily used to treat hypertriglyceridemia (i.e, Fredrickson Type IV and V) and/or mixed hyperlipidemia.

The PPARγ receptor subtypes are involved in activating the program of adipocyte differentiation and are not involved in stimulating peroxisome proliferation in the liver. There are two known protein isoforms of PPARγ:PPARγ1 and PPARγ2 which differ only in that PPARγ2 contains an additional 28 amino acids present at the amino terminus. The DNA sequences for the human isotypes are described in Elbrecht, et al., BBRC 224;431-437 (1996). In mice, PPARγ2 is expressed specifically in fat cells. Tontonoz et al., Cell 79: 1147-1156 (1994) provide evidence to show that one physiological role of PPARγ2 is to induce adipocyte differentiation. As with other members of the nuclear hormone receptor superfamily, PPARγ2 regulates the expression of genes through interaction with other proteins and binding to hormone response elements, for example in the 5' flanking regions of responsive genes. An example of a PPARγ2 responsive gene is the tissue-specific adipocyte P2 gene. Although peroxisome proliferators, including the fibrates and fatty acids, activate the transcriptional activity of PPAR's, only prostaglandin $J_2$ derivatives have been identified as potential natural ligands of the PPARγ subtype, which also binds thiazolidinedione antidiabetic agents with high affinity.

The human nuclear receptor gene PPARδ (hPPARδ) has been cloned from a human osteosarcoma cell cDNA library and is fully described in A. Schmidt et al., *Molecular Endocrinology*, 6:1634-1641 (1992). It should be noted that PPARδ is also referred to in the literature as PPARβ and as NUC1, and each of these names refers to the same receptor; in Schmidt et al. the receptor is referred to as NUC1.

In WO96/01430, a human PPAR subtype, hNUC1B, is disclosed. The amino acid sequence of hNUC1B differs from human PPARδ (referred to therein as hNUC1) by one amino acid, i.e., alanine at position 292. Based on in vivo experiments described therein, the authors suggest that hNUC1B protein represses hPPARα and thyroid hormone receptor protein activity.

It has been disclosed in WO97/28149 that agonists of PPARδ are useful in raising HDL plasma levels. PPARδ agonists have recently been disclosed in U.S. Provisional Application Ser. No. 60/297,356 as having utility in the treatment of various inflammatory diseases, such as rheumatoid arthritis. WO97/27857, 97/28115, 97/28137 and 97/27847 disclose compounds that are useful as antidiabetic, antiobesity, anti-atherosclerosis and antihyperlipidemic agents, and which activate PPARs.

It is generally believed that glitazones exert their effects by binding to the peroxisome proliferator activated receptor (PPAR) family of receptors, controlling certain transcription elements having to do with the biological entities listed above. Glitazones are benzyl-2,4-thiazolidinedione derivatives. See Hulin et al., Current Pharm. Design (1996) 2, 85-102.

A number of glitazones that are PPAR agonists have been approved for use in the treatment of diabetes. These include troglitazone, rosiglitazone and pioglitazone, all of which are primarily or exclusively PPARγ agonists. Many of the newer PPAR agonists that are currently under development or are in clinical trials have dual PPARα and γ activity, such as KRP-297. The PPARα/γ agonists are expected to improve both insulin sensitivity and the lipid profile in patients having NIDDM.

Although glitazones have been beneficial in the treatment of NIDDM, there have been some serious adverse events associated with the use of the compounds, especially troglitazone, which was eventually withdrawn. The most serious adverse events have been liver toxicity, which resulted in a number of deaths. Because of the problems that have occurred with the glitazones, researchers in a number of laboratories have been investigating classes of PPAR agonists that do not contain 1,3-thiazolidinedione moieties and therefore are not glitazones.

Compounds that are agonists of the various PPAR subtypes are expected to be useful in the treatment of diseases and conditions that respond to treatment with PPAR agonists, regardless of whether the compounds are glitazones. These include dyslipidemia, diabetes, and related conditions. PPARα agonists improve the lipid profile and alleviate dyslipidemias by reducing elevated LDL levels, reducing elevated triglyceride levels, and increasing HDL levels. PPARγ agonists improve insulin sensitivity, reducing the need for insulin secretagogues and insulin injections in patients with NIDDM. The role of PPARδ is less well defined, but PPARδ also appears to help control hyperlipidemia and hyperglycemia in type 2 diabetic patients.

SUMMARY OF THE INVENTION

The class of compounds described herein is a new class of potent PPARα agonists that do not contain a 1,3-thiazolidinedione moiety. They exhibit little or no activity at the PPARγ and PPARδ receptor, and they are therefore selective. Preferred compounds have a high affinity for the PPARα receptor, with an $IC_{50}$ less than 250 nM, using the PPARα binding assay. The compounds generally have an $IC_{50}$ greater than 15,000 in the PPARγ binding assay, and greater than 50,000 in the PPARδ binding assay. The compounds are useful in the treatment of diseases, disorders and conditions that are treated or ameliorated by PPARα agonists.

The compounds are useful in treating one or more of the following conditions: mixed or diabetic dyslipidemia; other lipid disorders, including isolated hypercholesterolemia as manifested by elevations in LDL-C and/or non-HDL-C; hyperapoBliproteinemia; hypertriglyceridemia; elevated triglyceride-rich-lipoproteins; and low HDL cholesterol concentrations. The compounds may also have utility in treating or ameliorating atherosclerosis, obesity, vascular restenosis, and inflammatory conditions. As a result of their utility in treating and ameliorating lipid disorders and obesity, and perhaps insulin resistance and/or hyperglycemia, the compounds of this invention also may be effective in treating or ameliorating the metabolic syndrome, also known as Syndrome X. They may also reduce the risk of developing atherosclerosis in a patient at risk of developing atherosclerosis by ameliorating some of the risk factors, such as those that are the criteria that define metabolic syndrome.

The present invention provides compounds having the structure of Formula I, including pharmaceutically acceptable salts and prodrugs of these compounds:

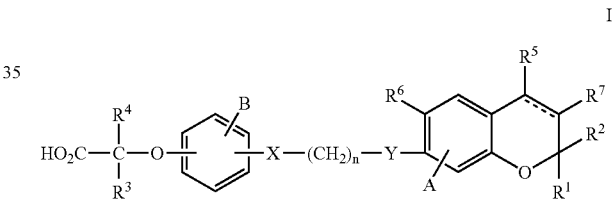

In the compounds of Formula I:
$R^1$ and $R^2$ are each $C_1$-$C_3$ alkyl, which are optionally substituted with 1-5 halogens independently selected from F and Cl;
$R^3$ is selected from the group consisting of
  (a) H, and
  (b) $C_1$-$C_3$alkyl, which is optionally substituted with 1-5 halogens independently selected from F and Cl;
$R^4$ is $C_1$-$C_3$ alkyl, which is optionally substituted with 1-5 halogens independently selected from F and Cl;
$R^5$ is selected from the group consisting of H and $C_1$-$C_3$alkyl, which is optionally substituted with 1-5 halogens independently selected from F and Cl;
$R^6$ is selected from H, Cl, $CH_3$ and $CF_3$;
$R^7$ is H or $C_1$-$C_3$ alkyl, which is optionally substituted with 1-5 halogens independently selected from F and Cl;
A and B are each independently selected from H, Cl, F, $CH_3$, and $CF_3$;
The dashed line connecting the ring carbon atoms attached to $R^5$ and $R^7$ is an optional double bond;
X and Y are each O or S; and
n is 2 or 3.

In the above summary, reference to alkyl groups by carbon number, such as $C_3$ alkyl or $C_{3-6}$ alkyl, refers to linear or branched alkyl.

The compounds described above are effective in treating diseases or conditions that respond to treatment with PPARα agonists. The compounds are expected to be efficacious in treating or ameliorating one or more of the following diseases or conditions: hyperlipidemia, dyslipidemia, hypercholesterolemia, hypertrigyceridemia, and obesity. Some of the compounds may also be efficacious in treating or ameliorating non-insulin dependent diabetes mellitus (NIDDM) in mammalian patients and human patients in need of treatment, and in the treatment and amelioration of conditions that are often associated with NIDDM, but which may also be present in non-diabetic patients, including hyperlipidemia, dyslipidemia, hypercholesterolemia, hypertrigyceridemia, and obesity. The compounds may also be effective in treating atherosclerosis, hyperinsulinemia, insulin resistance, vascular restenosis, and inflammatory conditions. The compounds may delay or reduce the risk of one or more of the sequelae of NIDDM, such as atherosclerosis, vascular restenosis, and retinopathy by ameliorating some of the conditions that contribute to the development of these diseases. They may also be effective in reducing cardiovascular events that occur in human patients having metabolic syndrome, such as coronary heart disease.

DETAILED DESCRIPTION OF THE INVENTION

The invention has numerous embodiments. Several preferred sub-groups of compounds are described below:

One embodiment is the sub-group of compounds having Formula I, where X and Y are each O.

Another embodiment is the sub-group of compounds having Formula I, where A, B, and $R^7$ are H.

Compounds of Formula I in which $R^5$ is $CF_3$ comprise another preferred sub-group of compounds of this invention.

Compounds of Formula I in which $R^5$ is $C_1$-$C_3$ alkyl are another preferred sub-group of compounds.

In another sub-group of compounds having Formula I, $R^6$ is selected from Cl, $CH_3$ and $CF_3$. In many preferred compounds of this sub-group, $R^6$ is Cl.

In another embodiment of compounds having Formula I, $R^3$ is H, $CH_3$, $C_2H_5$, or $C_3H_7$; and R4 is $CH_3$, $C_2H_5$, or $C_3H_7$. In a preferred sub-group, R3 and R4 are each selected from $CH_3$, $C_2H_5$, and $C_3H_7$.

In still another embodiment of compounds having Formula I, $R^1$ and $R^2$ each independently may be $CH_3$ or $C_2H_5$.

A preferred sub-group of compounds of Formula I comprises compounds in which $R^1$ and $R^2$ are each $CH_3$.

A preferred sub-set of compound having Formula I, including pharmaceutically acceptable salts, is described as follows:

$R^1$ and $R^2$ are each independently $CH_3$ or $C_2H_5$;
$R^3$ and R4 are each independently selected from $CH_3$, $C_2H_5$, and $C_3H_7$;
$R^5$ is $CF_3$;
$R^6$ is Cl;
$R^7$, A, and B are all H;
The dashed line connecting the ring carbon atoms that are attached to $R^5$ and $R^7$ is a double bond;
X and Y are O; and
n is 2 or 3.

A preferred subgroup of the compounds described immediately above comprises compounds having Formula I in which $R^1$ and $R^2$ are each $CH_3$.

Another preferred subgroup comprises compounds in which n is 3.

Specific examples of compounds of this invention are provided in Examples 1-9. These compounds are illustrated in the Table of Compounds immediately before the Examples.

The invention further includes pharmaceutical compositions comprising any of the compounds described herein, including pharmaceutically acceptable salts, and a pharmaceutically acceptable carrier.

Definitions

"Alkyl", as well as other groups having the prefix "alk", such as alkoxy or alkenyl, means carbon chains which may be linear or branched, including chains with multiple branch points, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Isopropyl and sec- and tert-butyl are branched.

"Alkenyl" means carbon chains which contain at least one carbon-carbon double bond, and which may be linear or branched. Examples of alkenyl include vinyl, allyl, isopropenyl, pentenyl, hexenyl, heptenyl, 1-propenyl, 2-butenyl, 2-methyl-2-butenyl, and the like.

"Cycloalkyl" means a mono- or bicyclic saturated carbocyclic ring having from 3 to 10 carbon atoms, unless otherwise stated. The term also includes a monocyclic or bicyclic saturated carbocyclic ring which is fused to another cyclic group, such as an aryl group. Examples of cycloalkyl include cyclopropyl, cyclopentyl, cyclohexyl, cycloheptyl, and the like.

"Aryl" (and "arylene") when used to describe a substituent or group in a structure means a monocyclic or bicyclic or tricyclic group or substituent in which all of the rings are aromatic and which contains only carbon ring atoms. "Aryl" groups can be fused to other cyclic groups, such as a cycloalkyl or heterocyclic group. Examples of aryl substituents include phenyl and naphthyl. Phenyl is the preferred aryl group.

"Heterocycle" means a fully or partially saturated ring containing at least one heteroatom selected from N, S and O, where the ring has from 3 to 10 atoms, unless otherwise defined.

"Heteroaryl" (and "heteroarylene") means an aromatic ring containing at least one ring heteroatom selected from N, O and S (including SO and $SO_2$), where the ring contains 5-6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, and pyrazinyl. Heteroaryl and aromatic rings can be fused together to form bicyclic or tricyclic ring systems, as for example benzisoxazolyl, benzoxazolyl, benzothiazolyl, benzimidazolyl, benzofuranyl, benzothiophenyl (including S-oxide and dioxide), quinolyl, indolyl, isoquinolyl, dibenzofuran and the like.

"Halogen" includes fluorine, chlorine, bromine and iodine. Fluorine is generally the most preferred halogen substituent on an alkyl group.

"Me" and "Et" represent methyl and ethyl respectively.

The term "administration of" or "administering" a compound means providing a compound of this invention or a prodrug of a compound of this invention to a patient in need of treatment.

The "patient" to whom the compounds of this invention can be administered may be selected from mammals, including primates, such as monkeys and apes; bovines, such as cows; equines, such as horses; canines, such as dogs; felines, such as cats; ovines, such as goats and sheep; and rodents, such as mice, rats, and guinea pigs. Patients may also include non-mammalian species, such as chickens and other birds. The preferred patient is a human.

To treat, as a disease or condition, means to deal with the disease or condition in a specified manner.

Amelioration of a disease or condition means improving the disease or condition or making it better.

"Metabolic Syndrome" is defined in the Third Report of the National Cholesterol Education Program Expert Panel on Detection, Evaluation and Treatment of High Blood Cholesterol In Adults (ATP-III). E. S. Ford et al., JAMA, vol. 287 (3), Jan. 16, 2002, pp 356-359. Briefly, a person is defined as having metabolic syndrome if the person has three or more of the the following symptoms: abdominal obesity, hypertriglyceridemia, low HDL cholesterol, high blood pressure, and high fasting plasma glucose. The criteria for these are defined in ATP-III.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers-Diastereomers-Geometric Isomers-Tautomers

Compounds of Formula I may contain one or more asymmetric centers. The compounds can thus occur as racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen coupled with double bond shifts, referred to as tautomers. An example is a carbonyl (e.g. a ketone) and its enol form, often known as keto-enol tautomers. The individual tautomers as well as mixtures thereof are encompassed with compounds of Formula I.

If desired, racemic mixtures of compounds of Formula I may be separated by means of classical resolution through fractional crystallization of salts formed with enantiomerically pure acids or bases. Other diasteromeric derivatives can be formed by the coupling of a racemic mixture of the compounds of Formula I to an enantiomerically pure compound. Such diastereomeric mixture may be separated by standard chromatographic methods or recrystallization protocols. These diasteromeric derivatives may then be converted to the pure enantiomers of the compounds of Formula I by cleavage of the added chiral residue. The racemic mixture of the compounds of Formula I can also be separated directly by chromatographic methods utilizing chiral stationary phases, of which many examples are known in the literature.

Alternatively, any enantiomer of a compound of the general Formula I may be obtained by stereoselective synthesis using optically pure starting materials or reagents of known configuration.

Compounds of Formula I that have more than one asymmetric center and that occur as diasteromeric mixtures can similarly be separated into individual diastereomers by standard methods, and these can be separated to individual enantiomers as described above.

Salts

The term "pharmaceutically acceptable salts" refers to salts prepared from pharmaceutically acceptable non-toxic bases or acids including inorganic or organic bases and inorganic or organic acids. For the carboxylic acid compounds of Formula I, salts derived from inorganic bases include aluminum, ammonium, calcium, copper, ferric, ferrous, lithium, magnesium, manganous, manganic, potassium, sodium, and zinc salts and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

For compounds that are basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites-Prodrugs

Prodrugs are compounds that are converted to the claimed compounds as they are being administered to a patient or after they have been administered to a patient. The prodrugs are compounds of this invention, and the active metabolites of the prodrugs, where the metabolites have Formula I, are also compounds of the invention. A non-limiting example of a prodrug of the carboxylic acids of this invention is an ester of the carboxylic acid, as for example a $C_1$ to $C_6$ ester, or an ester which has functionality that makes it more easily hydrolyzed after administration to a patient.

Examples of prodrugs of this class of compounds may be described as compounds having Formula Ia, where G is a group that is easily removed under

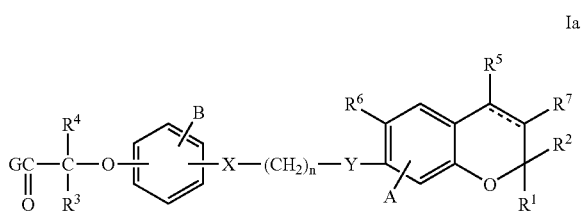

physiological conditions during or after administration to a mammalian patient to yield the free carboxylic acid or carboxylate salt thereof, where G has been converted to OH, or the carboxylate salt thereof. The other substituents in Formula Ia are as previously defined for Formula I.

Examples of prodrugs of Formula Ia include compounds in which G is selected from the group consisting of —OR$^a$, —OCH$_2$OR$^a$, —OCH(CH$_3$)OR$^a$, —OCH$_2$OC(O)R$^a$, —OCH(CH$_3$)OC(O)R$^a$, —OCH$_2$OC(O)OR$^a$, —OCH(CH$_3$)OC(O)OR$^a$, and —NR$^b$R$^b$, where each R$^a$ is independently selected from C$_{1-6}$ alkyl which is optionally substituted with one or two groups selected from —CO$_2$H, —CONH$_2$, —NH$_2$, —OH, —OAc, —NHAc, and phenyl; and wherein each R$^b$ is independently selected from H and R$^a$.

Utilities

Compounds of the present invention are potent agonists of the peroxisome proliferator activated receptor subtypes, particularly PPARα, with little or no activity with respect to PPARγ or PPARδ. Compounds of the present invention are thus selective and potent agonists of the subtype PPARα. Compounds of the present invention are useful in treating, controlling or ameliorating diseases, disorders and conditions, where the treatment, control or amelioration is effected by the activation of the PPARα subtype.

An important aspect of this invention is that it provides a method for the treatment, or amelioration of various lipid disorders, including dyslipidemia, hypercholesterolemia, hyperlipidemia, hypertriglyceridemia, low HDL levels, high LDL levels, and atherosclerosis and its sequelae, which comprises administering to a patient in need of such treatment a therapeutically effective amount of a compound having formula I.

The compounds as defined herein may be used in treating one or more of the following diseases or conditions in a mammalian or human patient in need of treatment, where the treatment comprises the administration of a therapeutically effective amount of a compound of Formula I to the patient in need of treatment:

(1) lipid disorders;
(2) hyperlipidemia;
(3) low HDL-cholesterol;
(4) high LDL-cholesterol;
(5) hypercholesterolemia;
(6) hypertriglyceridemia;
(7) dyslipidemia, including high LDL cholesterol and low HDL cholesterol; and
(8) atherosclerosis, including sequelae of atherosclerosis (angina, claudication, heart attack, stroke, etc.).

More generally, compounds having Formula I may be used to treat or ameliorate one or more of the following diseases, disorders and conditions: (1) lipid disorders, (2) dyslipidemia, (3) hyperlipidemia, (4) hypertriglyceridemia, (5) hypercholesterolemia, (6) low HDL levels, (7) high LDL levels, (8) atherosclerosis and its sequelae, (9) obesity, including abdominal obesity (10) vascular restenosis, (11) retinopathy, (12) non-insulin dependent diabetes mellitus (NIDDM), (13) hyperglycemia, (14) impaired glucose tolerance, (15) insulin resistance, (16) irritable bowel syndrome, (17) inflammatory bowel disease, including Crohn's disease and ulcerative colitis, (18) pancreatitis, (19) other inflammatory conditions, (20) neurodegenerative disease, (21) Alzheimer's disease, (22) psoriasis, (23) acne vulgaris, (24) other skin diseases and dermatological conditions modulated by PPAR, (25) high blood pressure, (26) cachexia, and (27) the metabolic syndrome, sometimes known as Syndrome X.

The compounds may also be useful in the treatment of (1) neoplastic conditions, (2) adipose cell tumors, (3) adipose cell carcinomas, such as liposarcoma, (4) prostate cancer and other cancers, including gastric, breast, bladder and colon cancers, and (5) angiogenesis.

Other conditions which may be treated with the compounds of this invention include ovarian hyperandrogenism (polycystic ovarian syndrome), cachexia, and other disorders where insulin resistance is a component.

The present invention is further directed to a method for the manufacture of a medicament that is useful for the treatment or control of a disease or condition that is treated by the administration of a PPARα agonist, wherein the method comprises combining an effective amount of the compound of Formula I with a pharmaceutically acceptable carrier or diluent.

Another aspect of the invention provides a method of treating cachexia. PPARα is known to be necessary for an appropriate energy sparing response to starvation, and inappropriate metabolism and energy utilization is clearly responsible for the wasting of cachexia. The compounds of this invention may therefore be useful in the treatment of cachexia.

In another aspect, the invention provides a method of treating inflammatory conditions, including inflammatory bowel disease, Crohn's disease, and ulcerative colitis, by administration of an effective amount of a PPARα agonist of Formula I. Additional inflammatory diseases that may be treated with the instant invention include gout, rheumatoid arthritis, osteoarthritis, multiple sclerosis, asthma, ARDS, psoriasis, vasculitis, ischemia/reperfusion injury, and related diseases.

Another aspect of the invention provides a method of treating a variety of skin diseases and dermatological conditions that are modulated by PPARα agonists by administering an effective amount of a compound of Formula I to a mammalian or human patient in need of such treatment. These diseases and conditions include psoriasis and acne vulgaris. Examples of other skin diseases and dermatological disorders that may be treated include eczema; lupus associated skin lesions; dermatitides such as seborrheic dermatitis and solar dermatitis; keratoses such as seborrheic keratosis, senile keratosis, actinic keratosis, photo-induced keratosis, and keratosis follicularis; keloids and prophylaxis against keloid formation, warts including verruca, condyloma, or condyloma accuminatum, and human papilloma viral (HPV) infections such as venereal warts, viral warts, molluscum contagiosum, leukoplakia, lichen planus, keratitis, skin cancer such as basal cell carcinoma, cutaneous T cell lymphoma and localized benign epidermal tumors (keratoderma, epidermal naevi).

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating hypertriglyceridemia, hypercholesterolemia, dyslipidemia, hyperlipidemia, and other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 1 milligram to about 350 milligrams. This dosage regimen will vary depending on the specific compound and also the patient. The dosage may be adjusted within the ranges recited above or even outside those ranges in order to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier and optionally other therapeutic ingredients. More typically, a selected compound of Formula I, or a pharmaceutically acceptable salt thereof, will be the only active ingredient in a composition. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compounds of this invention may be used in combination with other drugs that may also have utility in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

For example, the compounds of Formula I may be administered in combination with one or more other lipid lowering drugs, including (1) a cholesterol biosynthesis inhibitor, including but not limited to, an HMG-CoA reductase inhibitor, such as lovastatin, simvastatin, pravastatin, fluvastatin, atorvastatin, rivastatin, itavastatin, rosuvastatin, and ZD-4522; (2) a cholesterol absorption inhibitor (for example a stanol ester, a sterol glycoside such as tiqueside, or an azetidinone such as ezetimibe); (3) an ACAT inhibitor (such as avasimibe), (4) niacin; (5) a bile acid sequestrant; (6) a microsomal triglyceride transport inhibitor; (7) a bile acid reuptake inhibitor; and (8) a PPARα/γ agonist, such as KRP-297. These combination treatments are expected to be particularly effective for the treatment or control of one or more lipid disorders or conditions selected from dyslipidemia, hypercholesterolemia, hyperlipidemia, hypertriglyceridemia, low HDL levels, high LDL levels, and atherosclerosis and its sequelae. The combination therapy may make it possible to achieve therapeutic control using a reduced amount of one or both active ingredients and/or to achieve better lipid control than would be expected based on the control that is achieved when either of the compounds is used alone. The combination therapy may make it possible to achieve therapeutic control of one or more lipid disorders and diabetes. Preferred combinations include a compound of Claim 1 and one or more other compounds selected from a cholesterol absorption inhibitor, such as ezetimibe, a statin (e.g. simvastatin, atorvastatin, or rosuvastatin), an ACAT inhibitor, or another PPARα agonist, such as fenofibrate or another fibrate. Highly preferred combinations include combinations consisting essentially of a compound of this invention with a cholesterol absorption inhibitor (ezetimibe), or a compound of this invention with a statin (eg simvastatin), or a compound of this invention with both a statin and a cholesterol asorption inhibitor.

More generally, examples of therapeutic classes of compounds that may be administered in combination with a compound of Formula I, either separately or in the same pharmaceutical composition, include, but are not limited to:

(a) insulin sensitizers;
(b) antidiabetic compounds;
(c) cholesterol lowering agents;
(d) antiobesity compounds;
(e) anti-inflammatory compounds; and
(f) antihypertensives.

Examples of classes of compounds that may be administered in combination with compounds having Formula I include:

(a) PPARγ agonists and partial agonists, such as the glitazones (e.g. troglitazone, pioglitazone, englitazone, MCC-555, rosiglitazone, and the like);
(b) PPARα/γ dual agonists, such as KRP-297;
(c) other PPARα agonists, such as fenofibric acid derivatives, including gemfibrizol, clofibrate, fenofibrate, and bezafibrate,
(d) PPARδ agonists such as those disclosed in WO97/28149;
(e) biguanides, such as metformin and phenformin;
(f) protein tyrosine phosphatase-1B (PTP-1B) inhibitors;
(g) dipeptidyl peptidase IV (DP-IV) inhibitors;
(h) insulin or insulin mimetics;
(i) sulfonylureas, such as tolbutamide and glipizide, or related materials;
(j) α-glucosidase inhibitors (such as acarbose);
(k) glucagon receptor antagonists;
(l) glycogen phosphorylase inhibitors;
(m) 11-Beta-HSD type 1 enzyme inhibitors;
(n) 11-Beta-HSD type 1 receptor antagonists;
(o) exendin-4, exendin-3, GLP-1, GLP-1 mimetics, and GLP-1 receptor agonists, such as those disclosed in WO00/42026 and WO00/59887;
(p) GIP, GIP mimetics such as those disclosed in WO00/58360, and GIP receptor agonists;
(q) PACAP, PACAP mimetics, and PACAP receptor 3 agonists such as those disclosed in WO 01/23420;
(r) HMG-CoA reductase inhibitors (lovastatin, simvastatin, pravastatin, fluvastatin, atorvastatin, rivastatin, itavastatin, rosuvastatin, ZD-4522, and other statins);
(s) Bile acid sequestrants (cholestyramine, colestipol, and dialkylaminoalkyl derivatives of a cross-linked dextran);
(t) nicotinyl alcohol, nicotinic acid or a salt thereof;
(u) ezetimibe and other inhibitors of cholesterol absorption;
(v) acyl CoA:cholesterol acyltransferase inhibitors (ACAT inhibitors); such as for example avasimibe;
(w) phenolic anti-oxidants, such as probucol;
(x) ileal bile acid transporter inhibitors;
(y) agents intended for use in the treatment of inflammatory conditions such as aspirin, non-steroidal anti-inflammatory drugs, glucocorticoids, azulfidine, and cyclooxygenase 2 selective inhibitors;
(z) antiobesity compounds such as fenfluramine, dexfenfluramine, phentermine, sibutramine, orlistat, neuropeptide Y5 inhibitors, and $\beta_3$ adrenergic receptor agonists;
(aa) thyroid hormone mimetics;
(bb) LXR agonists;
(cc) FXR agonists;
(dd) PLTP inhibitors;
(ee) CETP inhibitors;
(ff) glucocorticoids; and
(gg) TNF sequestrants.

The above combinations will generally include combinations of one compound of the present invention with one other active compound. However, it is contemplated that combinations may also include more than two active ingredients, selected from one or more compounds of the present invention and one or more other active compounds listed above. Non-limiting examples include combinations of one or more compounds having Formula I with two or more active compounds selected from insulin sensitizers; antidiabetic compounds; cholesterol lowering agents; antiobesity compounds; anti-inflammatory compounds; and antihypertensives.

Examples of combinations that may be appropriate for patients having Type 2 diabetes accompanied by dyslipidemia include one or more compounds having Formula I and one or more compounds selected from anti-diabetic compounds, including biguanides, sulfonylureas, other PPARγ agonists, PTP-1B inhibitors, DP-IV inhibitors, insulin, and anti-obesity compounds.

Biological Assays

A) PPAR Binding Assays

For preparation of recombinant human PPARγ, PPARδ, and PPARα: Human PPARγ$_2$, human PPARδ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/m. aprotinin, 2 μg/mL leupeptin, 2 μg/mL benzamidine and 0.5 mM PMSF) containing 0.1% non-fat dry milk and 10 nM [$^3$H$_2$] AD5075, (21 Ci/mmole), ±test compound as described in Berger et al (Novel peroxisome proliferator-activated receptor (PPARγ) and PPARδ ligands produce distinct biological effects. J. Biol. Chem. (1999), 274: 6718-6725.) Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ±test compound as described in Berger et al (Novel peroxisome proliferator-activated receptors (PPARγ) and PPARδ ligands produce distinct biological effects. 1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$](3-(4-(3-phenyl-7-propyl-6-benz-[4,5]-isoxazoloxy)butyloxy))phenylacetic acid (34 Ci/mmole), ±test compound. This is a tritium labelled variant of Ex.62 in WO 97/28137. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B). Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at 12×10$^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% CO$_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate ±increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

C. In Vivo Studies

Male db/db mice (10-11 week old C57Bl/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose) ±test compound at the indicated dose. Drug suspensions were prepared daily. Plasma glucose, and triglyceride concentrations were determined from blood obtained by tail bleeds at 3-5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

Male Golden Syrian hamsters weighing ~150 g are used to measure lipid modulation effects of test compounds. Hamsters are housed in boxes (5 per box), are fed a normal rodent chow diet, and are given free access to water. Compounds are suspended in 0.5% methylcellulose and gavaged daily to the hamsters for 9 days (10 hamsters per group). On the morning of the 10$^{th}$ day, the hamsters are euthanized with carbon dioxide, and blood samples are obtained via heart puncture. Serum levels of total cholesterol and triglycerides determined.

Mature male beagle dogs, weighing ~15 kg on average, are used to measure the lipid modulation effects of test compounds. Dogs are housed individually, are fed a cholesterol-free chow diet, and are given free access to water. Prior to the start of experiments, samples are taken weekly from the jugular vein and the serum cholesterol levels are determined. To test the effects of compounds on serum cholesterol, compounds are suspended in 0.5% methylcellulose and gavaged daily to the dogs for 2 weeks (5 dogs per group). Blood samples are taken during and after the dosing period, and serum levels of total cholesterol and triglycerides are determined.

TABLE OF COMPOUNDS

The table below illustrates compounds that were synthesized in accordance with the present invention. Detailed syntheses are provided in the Examples.

Example 1

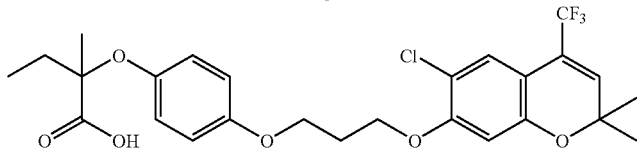

Example 2

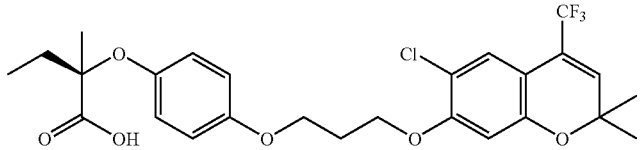

Example 3

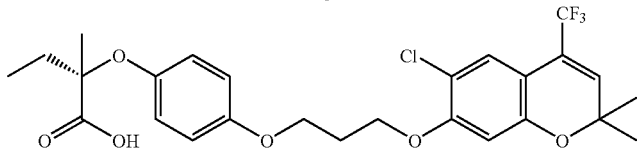

Example 4

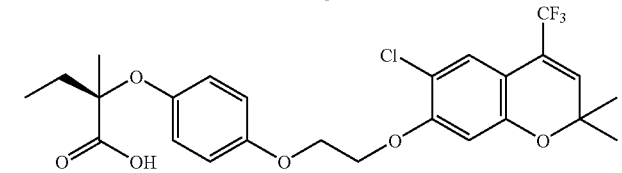

Example 5

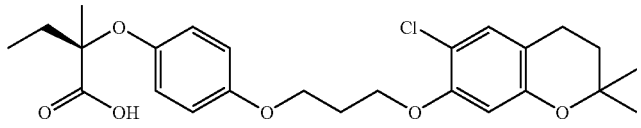

Example 6

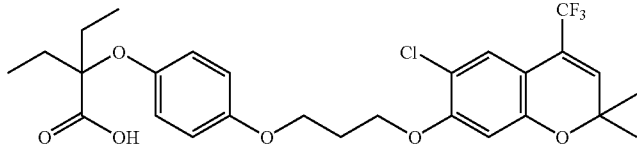

Example 7

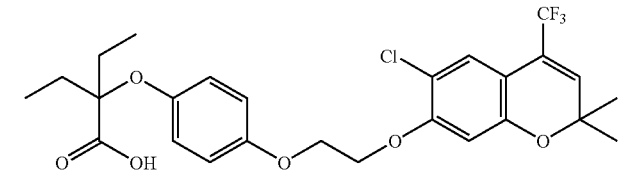

TABLE OF COMPOUNDS-continued

The table below illustrates compounds that were synthesized in accordance with the present invention. Detailed syntheses are provided in the Examples.

Example 8

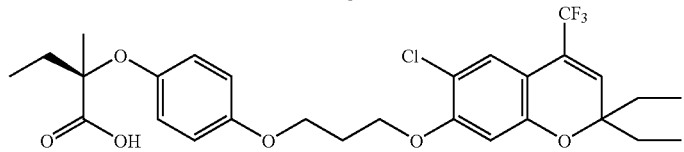

Example 9

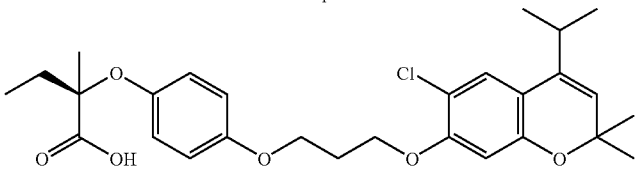

Synthetic Methods

The process for making the compounds of the instant invention is generally depicted in Scheme 1 below.

Note that the numbering of substituent groups used in the structures in Scheme I is different from the numbering in the generic description of the invention.

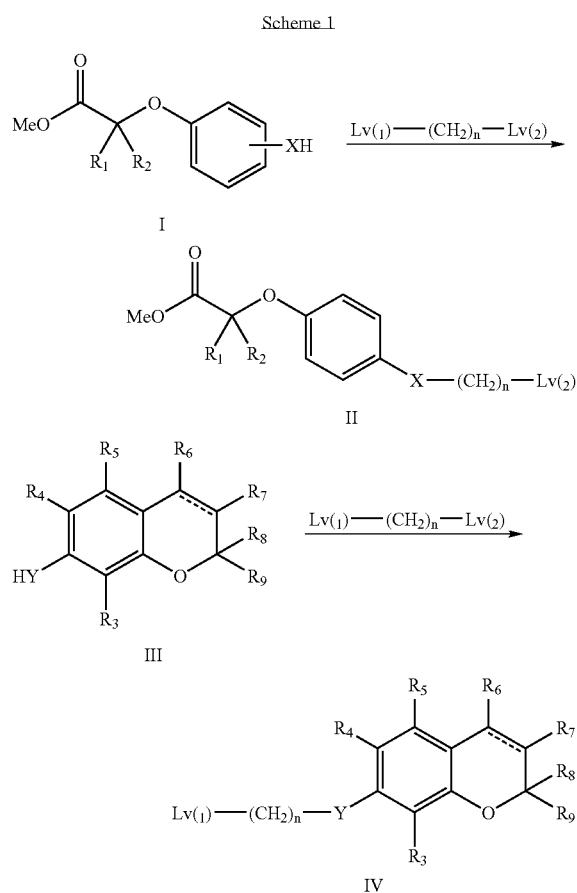

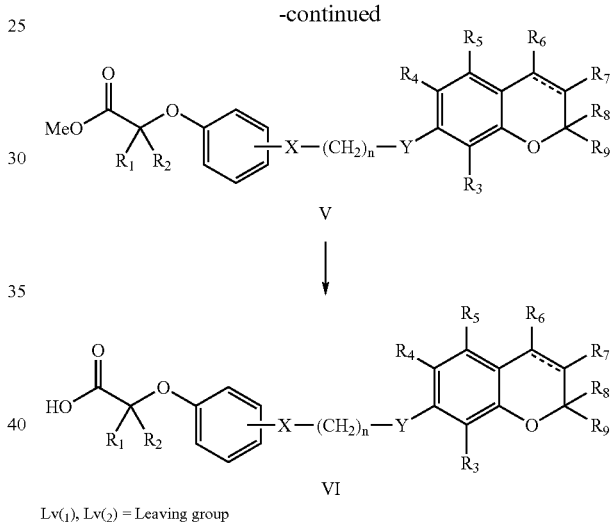

$Lv_{(1)}, Lv_{(2)}$ = Leaving group

The final compounds are assembled by the base-catalyzed coupling of chromen/chromanol precursors or the thiol analogs of these compounds (III) with precursors (II). Alternatively, these compounds are also available by coupling of precursors (I) and (IV). Coupling is carried out in the presence of an inorganic base (e.g. cesium carbonate) in DMF. The coupling can also be carried out under Mitsunobu reaction conditions. $Lv_{(1)}$ and $Lv_{(2)}$ are leaving groups well-known in the art, and preferably are independently selected from halogen, preferably iodine or bromine, or sulfonate such as methanesulfonate, or hydroxyl in the case of Mitsunobu reaction conditions. The desired carboxylic acids VI may be synthesized by ester hydrolysis of the compounds having formula V under aqueous basic (e.g. aq. KOH) conditions.

EXAMPLES

The following Examples are provided to illustrate the invention, including methods of making the compounds of the invention, and are not to be construed as limiting the invention in any manner. The scope of the invention is defined only by the appended claims.

Example 1

2-(4-(3-((6-Chloro-2,2-dimethyl-4-(trifluoromethyl)-2H-chromen-7-yl)oxy)propoxy)phenoxy)-2-methylbutanoic acid

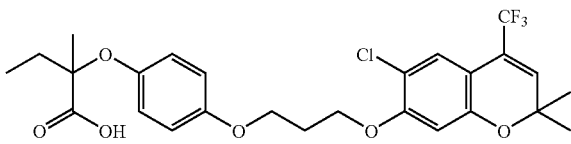

Step A: Methyl 2-(4-(benzyloxy)phenoxy)butanoate

A mixture of 4-benzyloxyphenol (30 g, 0.15 mol), cesium carbonate (58.6 g, 0.18 mol) and methyl 2-bromobutanoate (40.7 g, 0.22 mol) in $CH_3CN$ (350 mL) was kept at reflux for 20 hr. After cooling, the mixture was filtered and concentrated under reduced pressure and chromatographed over silica gel using AcOEt/hexanes to give the title compound 41.0 g (91%).

$^1$H-NMR (400 MHz, $CDCl_3$): δ 7.45-7.31 (m, 7H), 6.9 (d, 2H, J=9.2 Hz), 6.85 (d, 2H, J=9.2 Hz), 5.02 (s 2H), 4.45 (t, 1H, J=6.3 Hz), 3.76 (s, 3H), 1.98 (dq, 2H, J=7.4,6.3 Hz), 1.08 (t, 3H, J=7.4 Hz).

Step B: Methyl-(4-(benzyloxy)phenoxy)-2-methylbutanoate

To a 200 mL THF solution of methyl 2-(4-(benzyloxy)phenoxy)butanoate (30 g, 0.1 mol) was added at −78° C., a solution of lithium diisopropylamide (65 mL of 2 mol solution). After the addition was over, the resulting mixture was stirred at −78° C. for 30 min. To this was then added methyl iodide (15 mL) and stirring continued for 4 h during which the temperature was gradually allowed to rise. After quenching the reaction with sat.$NH_4Cl$ aq, the layers were separated and the aqueous layer was extracted with AcOEt and the combined organic phase washed with water, brine, dried over anhydrous $Na_2SO_4$ and concentrated to furnish the desired product (32 g). This product was used as such for the next step.

$^1$H-NMR (400 MHz, $CDCl_3$): δ 7.45-7.19 (m, 7H), 6.86 (d, 2H, J=9.3 Hz), 6.84 (d, 2H, J=9.2 Hz), 5.02 (s 2H), 3.79 (s, 3H), 1.97 (m, 2H), 1.45 (s, 3H), 0.99 (t, 3H, J=7.4 Hz).

Step C: Methyl 2-(4-hydroxyphenoxy)-2-methylbutanoate

A solution of methyl-(4-(benzyloxy)phenoxy)-2-methylbutanoate (32 g) in 100 mL MeOH was hydrogenated using 10% Pd/C at 40 psi. The mixture was filtered through a pad of celite to remove the catalyst. The filtrate was concentrated to afford thick oily residue (21 g, quantitative).

$^1$H-NMR (400 MHz, $CDCl_3$): δ 6.78 (d, 2H, J=9.0 Hz), 6.72 (d, 2H, J=9.0 Hz), 4.08 (s 1H), 3.79 (s, 3H), 1.98 (m, 2H), 1.43 (s, 3H), 0.99 (t, 3H, J=7.4 Hz).

Step D: Methyl 2-(4-(3-hydroxypropoxy)phenoxy)-2-methylbutanoate

To a solution of methyl 2-(4-hydroxyphenoxy)-2-methylbutanoate (5 g, 22.32 mmol) in 30 mL DMF was added cesium carbonate (8.7 g, 26.7 mmol) followed by benzyl 3-bromopropyl ether (7.7 g, 33.6 mmol). The solution was stirred at 45° C. for 24 hr, cooled and poured over water. Extraction with AcOEt followed by washing the extracts with water, drying over anhydrous $Na_2SO_4$ and concentrating under reduced pressure gave the crude residue. Purification over silica gel using AcOEt/hexanes furnished the desired alkylated derivative (8.25 g). This product was taken up in MeOH (75 mL) and hydrogenated over 10% Pd/C at 40 psi to provide methyl 2-(4-(3-hydroxypropoxy)phenoxy)-2-methylbutanoate (6.23 g, quantitative).

$^1$H-NMR (400 MHz, $CDCl_3$): δ 6.82 (d, 2H, J=9.4 Hz), 6.78 (d, 2H, J=9.2 Hz), 4.08 (t, 2H, J=6.1 Hz), 3.87 (t, 2H, J=6 Hz), 3.79 (s, 3H), 2.06-1.92 (m, 4H), 1.44 (s, 3H), 0.99 (t, 3H, J=7.4 Hz).

Step E: 6-Chloro-2,2-dimethyl-4-(trifluoromethyl)-2H-chromen-7-ol

To a solution of 6-chloro-7-hydroxy-4-(trifluoromethyl)-2H-chromen-2-one (1.5 g, 5.68 mmol) in anhydrous THF (25 mL) was added at 0° C. a solution of methyl magnesium chloride in THF (9.48 mL of 3 mol solution). After stirring at 0° C. for 1 h, the reaction was quenched with sat.$NH_4Cl$ aq. The organic layer was separated, washed with water, dried over anhydrous $Na_2SO_4$ and concentrated to provide the crude product. This was dissolved in toluene (50 mL) and to this was added p-toluenesulfonic acid (40 mg) and the solution was kept at reflux for 1 h with the azeotropic removal of water using Dean-Stark apparatus. The solution washed once with water, dried over anhydrous $Na_2SO_4$ and concentrated to give brownish residue which was subjected to purification over silica gel using AcOEt/hexanes to provide the desired product (1.3 g, 83%).

$^1$H-NMR (400 MHz, $CDCl_3$): δ 6.56 (s, 1H), 6.09 (s, 1H), 5.63 (s, 1), 1.48 (s, 6H).

Step F: Methyl 2-(4-(3-((6-chloro-2,2-dimethyl-4-(trifluoromethyl)-2H-chromen-7-yl)oxy)propoxy)phenoxy)-2-methylbutanoate To a solution of 6-Chloro-2,2-dimethyl-4-(trifluoromethyl)-2H-chromen-7-ol (0.66 g, 2.95 mmol), methyl 2-(4-(3-hydroxypropoxy)phenoxy)-2-methylbutanoate (1.0 g, 2.97 mmol) and triphenylphosphine (0.85 g, 3.24 mmol) in 25 mL THF is added diethyl azodicarboxylate (0.56 g, 3.21 mmol)(slight exotherm) and the reaction mixture is stirred at ambient temperature overnight (16 h). After concentrating under reduced pressure, the residue obtained is chromatographed over silica gel to provide methyl 2-(4-(3-((6-chloro-2,2-dimethyl-4-(trifluoromethyl)-2H-chromen-7-yl)oxy)propoxy)phenoxy)-2-methylbutanoate (0.99 g).

$^1$H-NMR (400 MHz, $CDCl_3$): δ 7.3(s, 1H), 6.81 (q, 4H, J=3 Hz), 6.82 (d, 2H, J=7.5 Hz), 6.51 (s, 1H), 6.06 (s, 1H), 4.19 (t, 2H, J=6.1 Hz), 4.14 (t, 2H, J=6.1 Hz), 3.79 (s, 3H), 2.29 (m, 2H), 1.95 (m, 2H), 1.47 (s, 6H), 1.43 (s, 3H), 0.99 (t, 3H, J=7.5 Hz).

Step G: 2-(4-(3-((6-Chloro-2,2-dimethyl-4-(trifluoromethyl)-2H-chromen-7-yl)oxy)propoxy)phenoxy)-2-methylbutanoic acid The above ester is dissolved in MeOH (10 mL) and treated with 50% NaOH aq (2 mL) at room temperature overnight (15 h), concentrated and acidified with 2N HCl aq. The aqueous solution is extracted with AcOEt, dried over anhydrous $Na_2SO_4$ and concentrated to give 0.73 g of the title compound.

$^1$H-NMR (400 MHz, $CDCl_3$): δ 7.3(s, 1H), 6.92 (d, 2H, J=9.2 Hz), 6.84 (d, 2H, J=9.0 Hz), 6.51 (s, 1H), 6.06 (s, 1H), 4.2 (t, 2H, J=6.0 Hz), 4.17 (t, 2H, J=6.0) 2.31(m, 2H), 1.99-1.8 (m, 2H), 1.47 (s, 6H), 1.06(t, 3H, J=7.4 Hz). MS m/e=529 ($M^+$+H).

Example 2

(2R)-2-(4-(3-((6-Chloro-2,2-dimethyl-4-(trifluoromethyl)-2H-chromen-7-yl)oxy)propoxy)phenoxy)-2-methylbutanoic acid

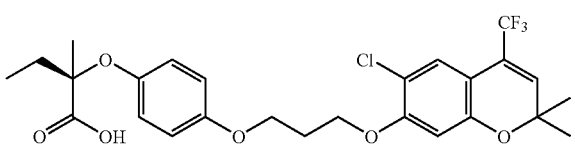

Step A:

1) Resolution of the racemic methyl 2-(4-hydroxyphenoxy)-2-methylbutanoate

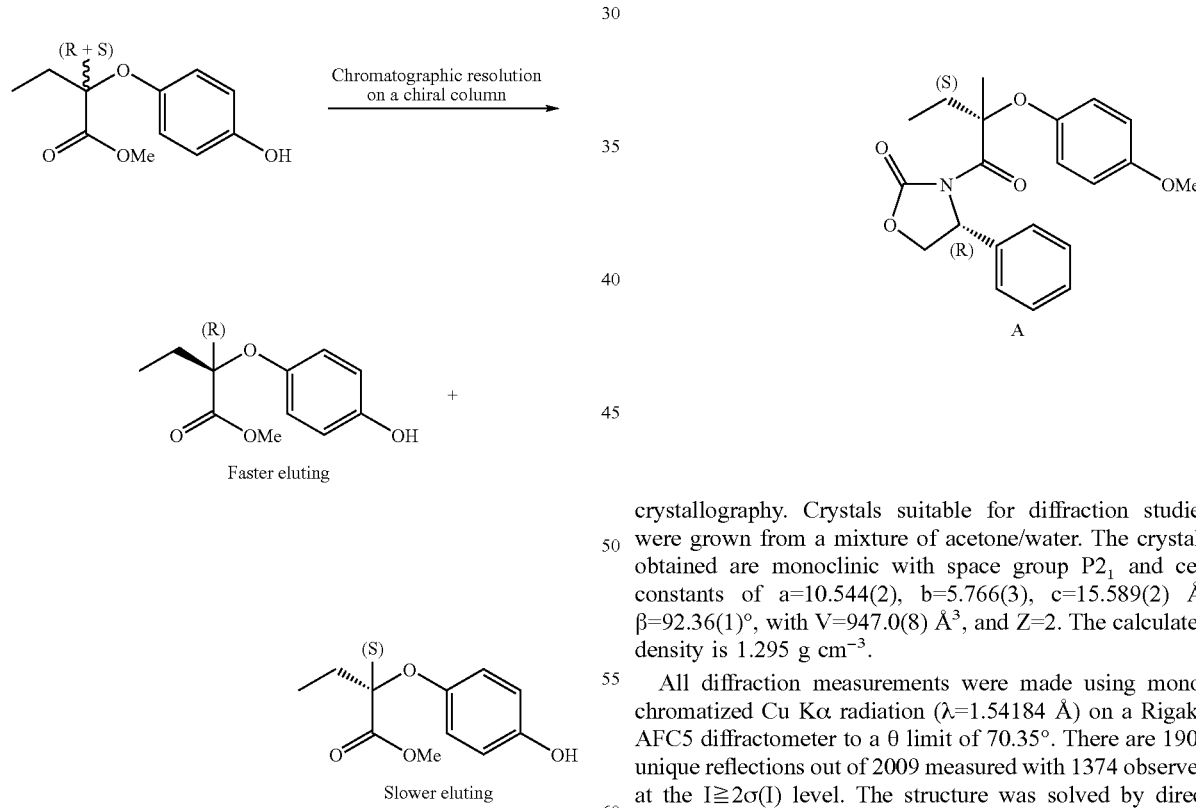

The racemic methyl 2-(4-hydroxyphenoxy)-2-methylbutanoate (144 g) prepared according to Example 1, Steps A-C was resolved on a preparatory scale using Chiaracel OJ (3 kg-gel) packed in a 6"×22" column. Elution with 30% EtOH-70% heptane gave the faster eluting (R) isomer (67.6 g) and slower eluting (S) isomer (49.5 g). On an analytical Chiracel OJ column (4.6 mm×250 mm, 20% EtOH-80% heptane, flow rate 1 ml/min, (+) CD deflection at 254 nm), the faster eluting (R) isomer had a RT=13.31 min and the slower eluting (S) isomer had a RT=18.86 min.

2) Determination of Absolute Stereochemistry

The slower moving isomer obtained as described above was converted to (2R)-2-phenyloxazolinone amide A. The stereochemistry at the chiral center of the isomer A was found to be (S) by X-ray crystallography. This means that the faster eluting isomer has (R) configuration at the chiral center.

The structure of the isomer A has been determined by single crystal X-Ray

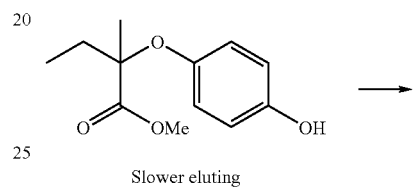

crystallography. Crystals suitable for diffraction studies were grown from a mixture of acetone/water. The crystals obtained are monoclinic with space group $P2_1$ and cell constants of a=10.544(2), b=5.766(3), c=15.589(2) Å, $\beta$=92.36(1)°, with V=947.0(8) Å$^3$, and Z=2. The calculated density is 1.295 g cm$^{-3}$.

All diffraction measurements were made using monochromatized Cu K$\alpha$ radiation ($\lambda$=1.54184 Å) on a Rigaku AFC5 diffractometer to a $\theta$ limit of 70.35°. There are 1908 unique reflections out of 2009 measured with 1374 observed at the I≧2$\sigma$(I) level. The structure was solved by direct methods and refined using full-matrix least-squares on F$^2$ using 244 parameters and all unique reflections. The refinement converged with agreement statistics of R=0.063, wR=0.190, S=1.06 with ($\Delta/\sigma)_{max}$<0.01.

A computer-generated perspective view of the molecule is shown in FIG. 1. Lists of interatomic distances and angles are given in Tables 1 and 2, respectively.

FIG. 1

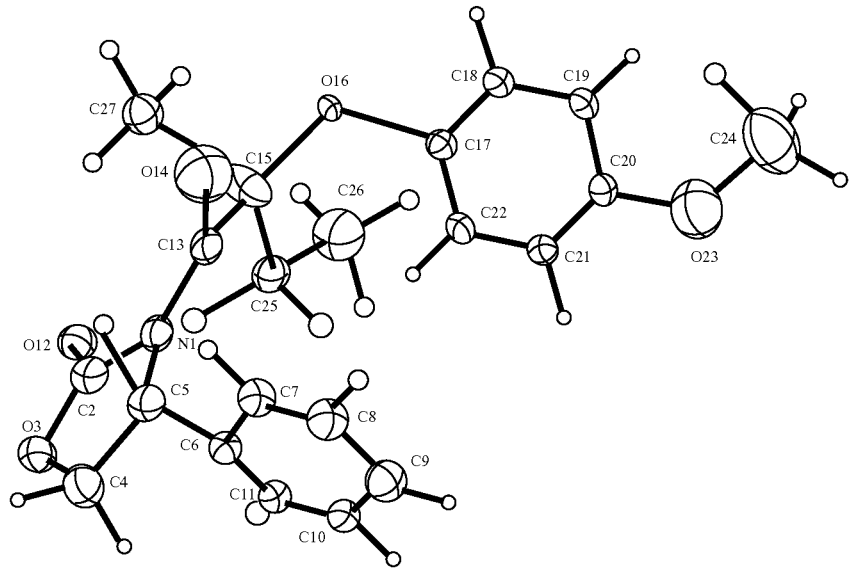

TABLE 1

Interatomic Distances (Å)

| | | | |
|---|---|---|---|
| O3—C2 | 1.334(8) | C7—C8 | 1.365(9) |
| O3—C4 | 1.424(8) | C8—C9 | 1.389(12) |
| O12—C2 | 1.188(7) | C9—C10 | 1.360(12) |
| O14—C13 | 1.188(8) | C10—C11 | 1.376(10) |
| O16—C17 | 1.378(7) | C13—C15 | 1.561(9) |
| O16—C15 | 1.428(8) | C15—C25 | 1.517(11) |
| O23—C20 | 1.376(8) | C15—C27 | 1.537(9) |
| O23—C24 | 1.394(13) | C17—C18 | 1.372(10) |
| N1—C2 | 1.396(8) | C17—C22 | 1.397(10) |
| N1—C13 | 1.409(9) | C18—C19 | 1.382(10) |
| N1—C5 | 1.480(7) | C19—C20 | 1.375(10) |
| C4—C5 | 1.532(10) | C20—C21 | 1.383(11) |
| C5—C6 | 1.497(8) | C21—C22 | 1.371(9) |
| C6—C11 | 1.385(9) | C25—C26 | 1.510(10) |
| C6—C7 | 1.413(9) | | |

TABLE 2

Interatomic Angles (deg.)

| | | | |
|---|---|---|---|
| C2—O3—C4 | 110.8(5) | O14—C13—N1 | 119.6(6) |
| C17—O16—C15 | 122.4(5) | O14—C13—C15 | 119.3(7) |
| C20—O23—C24 | 117.9(7) | N1—C13—C15 | 121.0(6) |
| C2—N1—C13 | 126.1(5) | O16—C15—C25 | 111.9(5) |
| C2—N1—C5 | 110.0(5) | O16—C15—C27 | 102.9(5) |
| C13—N1—C5 | 117.0(6) | C25—C15—C27 | 111.1(6) |
| O12—C2—O3 | 121.5(6) | O16—C15—C13 | 107.6(5) |
| O12—C2—N1 | 128.5(6) | C25—C15—C13 | 115.0(6) |
| O3—C2—N1 | 109.9(5) | C27—C15—C13 | 107.5(5) |
| O3—C4—C5 | 106.4(5) | C18—C17—O16 | 115.7(6) |
| N1—C5—C6 | 113.7(4) | C18—C17—C22 | 118.0(6) |
| N1—C5—C4 | 100.4(5) | O16—C17—C22 | 126.4(6) |
| C6—C5—C4 | 114.1(6) | C17—C18—C19 | 121.0(7) |
| C11—C6—C7 | 118.2(6) | C20—C19—C18 | 120.8(7) |
| C11—C6—C5 | 121.4(6) | C19—C20—O23 | 125.3(7) |
| C7—C6—C5 | 120.4(6) | C19—C20—C21 | 118.7(6) |
| C8—C7—C6 | 120.3(6) | O23—C20—C21 | 116.1(7) |
| C7—C8—C9 | 120.6(8) | C22—C21—C20 | 120.6(7) |
| C10—C9—C8 | 119.1(6) | C21—C22—C17 | 120.9(7) |

TABLE 2-continued

Interatomic Angles (deg.)

| | | | |
|---|---|---|---|
| C9—C10—C11 | 121.5(7) | C26—C25—C15 | 114.8(7) |
| C10—C11—C6 | 120.3(7) | | |

Step B: (2R)-2-(4-(3-((6-Chloro-2,2-dimethyl-4-(trifluoromethyl)-2H-chromen-7-yl)oxy)propoxy)phenoxy)-2-methylbutanoic acid As described in Example 1, Step D and F-G the title compound was prepared using (2R)-methyl 2-(4-(3-hydroxypropoxy)phenoxy)-2-methylbutanoate and 6-Chloro-2,2-dimethyl-4-(trifluoromethyl)-2H-chromen-7-ol.

$^1$H-NMR (400 MHz, CDCl$_3$): δ 7.3(s, 1H), 6.92 (d, 2H, J=9.2 Hz), 6.84 (d, 2H, J=9.0 Hz), 6.51 (s, 1H), 6.06 (s, 1H), 4.2 (t, 2H, J=6.0 Hz), 4.17 (t, 2H, J=6.0 Hz), 2.31(m, 2H), 1.99-1.8 (m, 2H), 1.47 (s, 6H), 1.06(t, 3H, J=7.4 Hz). MS m/e=529 (M$^+$+H).

Example 3

(2S)-2-(4-(3-((6-Chloro-2,2-dimethyl-4-(trifluoromethyl)-2H-chromen-7-yl)oxy)propoxy)phenoxy)-2-methylbutanoic acid

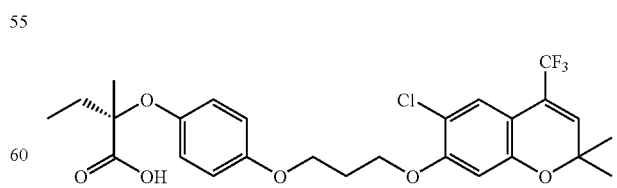

STEP A: 3-((6-chloro-2,2-dimethyl-4-(trifluoromethyl)-2H-chromen-7-yl)oxy)propan-1-ol To a solution of 6-Chloro-2,2-dimethyl-4-(trifluoromethyl)-2H-chromen-7-ol (10 g, 36.23 mmol) in 150 mL DMF was added cesium carbonate (24.8 g, 76.11 mmol) followed by 3-bromo-1-propanol (7.6 g, 54.3 mmol) and the mixture stirred at ambient temperature for 24 h. Dilution with water followed by extraction with AcOE and washing the organic extracts with water, drying over anhydrous Na$_2$SO$_4$ and finally concentrating under reduced pressure gave crude alkylated product. Purification over silica gel using AcOEt/hexanes provided the desired 3-((6-chloro-2, 2-dimethyl-4-(trifluoromethyl)-2H-chromen-7-yl)oxy)propan-1-ol (9.5 g, 78%).

$^1$H-NMR (400 MHz, CDCl$_3$): δ 7.32(s, 1H), 6.92 (d, 2H, J=9.2 Hz), 6.51 (s, 1H), 6.07 (s, 1H), 4.19 (t, 2H, J=5.7 Hz), 3.92 (t, 2H, J=5.5 Hz), 2.12(m, 2H), 1.48 (s, 6H).

STEP B: (2S)-Methyl 2-(4-(3-((6-Chloro-2,2-dimethyl-4-(trifluoromethyl)-2H-chromen-7-yl)oxy)propoxy)phenoxy)-2-methylbutanoate To a solution of 3-((6-chloro-2,2-dimethyl-4-(trifluoromethyl)-2H-chromen-7-yl)oxy)propan-1-ol (0.5 g, 1.48 mmol), (2S)-Methyl 2-(4-hydroxyphenoxy)-2-methylbutanoate (0.35 g, 1.56 mmol), and triphenylphosphine (0.42 g, 1.6 mmol) in THF (20 mL) was added diethyl azodicarboxylate (0.28 g, 1.6 mmol) and the solution stirred at ambient temperature for 16 h. After concentrating under reduced pressure, the residue thus obtained was chromatographed over silica gel using AcOEt/hexanes to furnish the desired compound (0.49 g).

$^1$H-NMR (400 MHz, CDCl$_3$): δ 7.3(s, 1H), 6.83 (d, 2H, J=9.2 Hz), 6.81 (d, 2H, J=9.2 Hz), 6.51 (s, 1H), 6.06 (s, 1H), 4.2 (t, 2H, J=6.1 Hz), 4.15 (t, 2H, J=6.1 Hz), 3.79 (s, 3H), 2.29(m, 2H), 1.99-1.8 (m, 2H), 1.47 (s, 6H), 1.44 (s, 3H), 0.99 (t, 3H, J=7.4 Hz).

STEP C: (2S)-2-(4-(3-((6-Chloro-2,2-dimethyl-4-(trifluoromethyl)-2H-chromen-7-yl)oxy)propoxy)phenoxy)-2-methylbutanoic acid The above ester was hydrolyzed with 50% NaOH aq (1 mL) in MeOH (10 mL) to give 0.45 g of the title compound.

$^1$H-NMR (400 MHz, CDCl$_3$): δ 7.3 (s, 1H), 6.92 (d, 2H, J=9.2 Hz), 6.84 (d, 2H, J=9.0 Hz), 6.51 (s, 1H), 6.06 (s, 1H), 4.2 (t, 2H, J=6.0 Hz), 4.17 (t, 2H, J=6.0 Hz), 2.31(m, 2H), 1.99-1.8 (m, 2H), 1.47 (s, 6H), 1.06(t, 3H, J=7.4 Hz). MS m/e=529 (M$^+$+H).

Example 4

(2R)-2-(4-(3-((6-Chloro-2,2-dimethyl-4-(trifluoromethyl)-2H-chromen-7-yl)oxy)ethoxy)phenoxy)-2-methylbutanoic acid

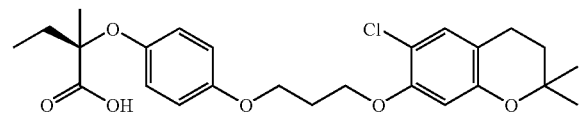

Step A: (2R)-Methyl 2-(4-(3-hydroxyethoxy)phenoxy)-2-methylbutanoate

Using benzyl 2-bromoethylether in place of benzyl 3-bromopropyl ether, (2R)-methyl 2-(4-hydroxyphenoxy)-2-methylbutanoate was converted to the desired (2R)-methyl 2-(4-(3-hydroxyethoxy)phenoxy)-2-methylbutanoate as described in Example 1, Step D.

$^1$H-NMR (400 MHz, CDCl$_3$): δ 6.84 (d, 2H, J=9.4 Hz), 6.81 (d, 2H, J=9.4 Hz), 4.04 (t, 2H, J=4.3 Hz), 3.94 (t, 2H, J=4.3 Hz), 3.79 (s, 3H), 1.96 (m, 2H), 1.44 (s, 3H), 0.99 (t, 3H, J=7.6 Hz).

Step B: (2R)-2-(4-(3-((6-Chloro-2,2-dimethyl-4-(trifluoromethyl)-2H-chromen-7-yl)oxy)ethoxy)phenoxy)-2-methylbutanoic acid The title compound was prepared following the procedure described in Example 1, Steps F-G employing (2R)-methyl 2-(4-(3-hydroxyethoxy)phenoxy)-2-methylbutanoate and 6-chloro-2,2-dimethyl-4-(trifluoromethyl)-2H-chromen-7-ol.

$^1$H-NMR (400 MHz, CDCl$_3$): δ 7.33(s, 1H), 6.9 (bs, 4H), 6.56 (s, 1H), 6.09 (s, 1H), 4.35 (s, 4H), 2.02-1.86 (m, 2H), 1.49 (s, 6H), 1.43 (s, 3H), 1.08 (t, 3H, J=7.3 Hz). MS m/e=515 (M$^+$+H).

Example 5

(2R)-2-(4-(3-((6-Chloro-2,2-dimethyl-3,4-dihydro-2H-chromen-7-yl)oxy)propoxy)phenoxy)-2-methylbutanoic acid

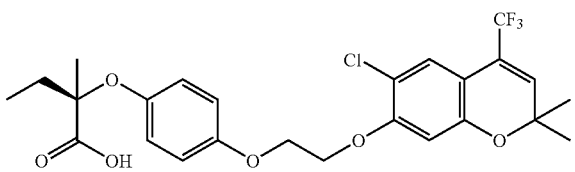

STEP A: 6-Chloro-2,2-dimethylchroman-7-ol

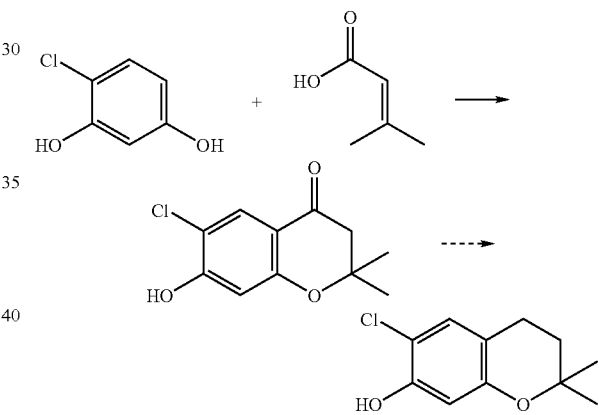

The desired 6-chloro-2,2-dimethylchroman-7-ol was synthesized from 4-chlororesorcinol as follows. A mixture of 3,3-dimethylacrylic acid (7.0 g) and 4-chlororesorcinol (10 g) in Eaton's reagent (50 mL) was stirred at ambient temperature for 16 h. At the end, the mixture was poured over ice and the precipitate was filtered, dried and crystallized from aqueous methanol to provide 6-chloro-7-hydroxy-2,2-dimethyl-2,3-dihydro-4H-chomen-4-one (8.7 g).

$^1$H-NMR (400 MHz, CDCl$_3$): δ 7.88(s, 1H), 6.58 (s, 1H), 6.01 (s, 1H), 2.69 (s, 2H), 1.47 (s, 6H).

The above phenol (2.2 g) was converted to the corresponding benzyloxy derivative using benzyl bromide and the product was reduced with NaBH$_4$ in MeOH to provide the alcohol which was then treated with conc. HCl in THF to provide the elimination derivative. Hydrogenation of this compound using Pd/C catalyst in AcOEt afforded the target 6-chloro-2,2-dimethylchroman-7-ol (1.55 g).

$^1$H-NMR (400 MHz, CDCl$_3$): δ 7.0(s, 1H), 6.47 (s, 1H), 5.3 (s, 1H), 2.69 (t, 2H, J=6.7 Hz), 1.78 (t, 2H, J=6.7 Hz), 1.33 (s, 6H).

STEP B: (2R)-2-(4-(3-((6-Chloro-2,2-dimethyl-3,4-dihydro-2H-chromen-7-yl)oxy)propoxy)phenoxy)-2-methylbutanoic acid The title compound was prepared following the procedure described in Example 1, Steps F-G employing (2R)-methyl 2-(4-(3-hydroxypropoxy)phenoxy)-2-methylbutanoate and 6-Chloro-2,2-dimethylchroman-7-ol.

$^1$H-NMR (400 MHz, CDCl$_3$): δ 7.04(s, 1H), 6.92 (d, 2H, J=9.2 Hz), 6.84 (d, 2H, J=9.0 Hz), 6.42 (s, 1H), 4.15 (m, 4H), 2.69 (t, 2H, J=6.7 Hz), 2.28 (m, 2H), 2-1.8 (m, 2H), 1.78 (t, 2H, J-6.9 Hz), 1.42 (s, 3H), 1.33 (s, 6H), 1.07 (t, 3H, J=7.4 Hz).

Example 6

2-(4-(3-((6-Chloro-2,2-dimethyl-4-(trifluoromethyl)-2H-chromen-7-yl)oxy)propoxy)phenoxy)-2-ethylbutanoic acid

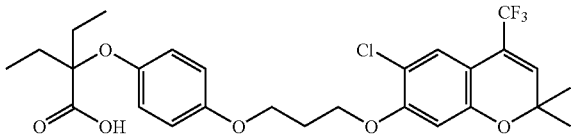

STEP A: Methyl 2-(4-(3-hydroxypropoxy)phenoxy)-2-ethylbutanoate

Using ethyl trifluoromethanesulfonate in place of methyl iodide in the alkylation of methyl 2-(4-(benzyloxy)phenoxy)butanoate and following the same procedure as described in Example 1, Step B-D, the target compound methyl 2-(4-(3-hydroxypropoxy)phenoxy)-2-ethylbutanoate was prepared.

$^1$H-NMR (400 MHz, CDCl$_3$): δ 6.83 (d, 2H, J=9.4 Hz), 6.79 (d, 2H, J=9.0Hz), 4.09 (t, 2H, J=6.0 Hz), 3.87 (t, 2H, J=5.7 Hz), 3.79 (s, 3H), 2.1-1.9 (m, 6H), 0.9 (t, 6H, J=7.5 Hz).

STEP B: 2-(4-(3-((6-Chloro-2,2-dimethyl-4-(trifluoromethyl)-2H-chromen-7-yl)oxy)propoxy)phenoxy)-2-ethylbutanoic acid Following the procedure described in Example 1, Step F-G the title compound was prepared using methyl 2-(4-(3-hydroxypropoxy)phenoxy)-2-ethylbutanoate and 6-chloro-2,2-dimethyl-4-(trifluoromethyl)-2H-chromen-7-ol.

$^1$H-NMR (400 MHz, CDCl$_3$): δ 7.31(s, 1H), 6.95 (d, 2H, J=9.2 Hz), 6.86 (d, 2H, J=9.0 Hz), 6.51 (s, 1H), 6.06 (s, 1H), 4.2-4.1 (m, 4H), 2.31(m, 2H), 2.0-1.8 (m, 4H), 1.47 (s, 6H), 0.99(t, 3H, J=7.2 Hz).

Example 7

2-(4-(3-((6-Chloro-2,2-dimethyl-4-(trifluoromethyl)-2H-chromen-7-yl)oxy)ethoxy)phenoxy)-2-ethylbutanoic acid

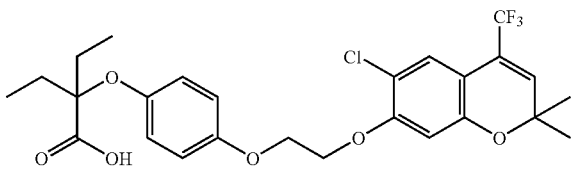

The title compound was prepared as described in Example 1, Step F-G using methyl 2-(4-(3-hydroxyethoxy)phenoxy)-2-ethylbutanoate and 6-chloro-2,2-dimethyl-4-(trifluoromethyl)-2H-chromen-7-ol.

$^1$H-NMR (400 MHz, CDCl$_3$): δ 7.33(s, 1H), 6.97 (d, 2H, J=9.1 Hz), 6.92 (d, 2H, J=9.1 Hz), 6.57 (s, 1H), 6.09 (s, 1H), 4.36 (s, 4H), 2.0-1.8 (m, 4H), 1.49 (s, 6H), 1.0(t, 3H, J=7.3 Hz).

Example 8

(2R)-2-(4-(3-((6-Chloro-2,2-diethyl-4-(trifluoromethyl)-2H-chromen-7-yl)oxy)propoxy)phenoxy)-2-methylbutanoic acid

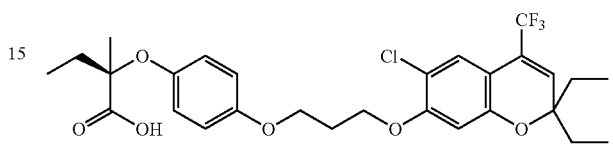

STEP A: 6-Chloro-2,2-diethyl-4-(trifluoromethyl)-2H-chromen-7-ol

This compound was prepared in an analogous manner as described for the preparation of the corresponding 6-Chloro-2,2-dimethyl-4-(trifluoromethyl)-2H-chromen-7-ol, Example 1, Step E substituting ethyl magnesium chloride in place of methyl magnesium chloride.

$^1$H-NMR (400 MHz, CDCl$_3$): δ 7.25 (s, 1H), 6.57 (s, 1H), 6.01 (s, 1H), 5.65 (s, 1H), 1.83-1.63 (m, 4H), 0.95 (t, 6H, J=7.4 H).

Step B: 2-(4-(3-((6-Chloro-2,2-diethyl-4-(trifluoromethyl)-2H-chromen-7-yl)oxy)propoxy)phenoxy)-2-methylbutanoic acid, Following the procedure described in Example 1, Step F-G the title compound was prepared using 6-chloro-2,2-diethyl-4-(trifluoromethyl)-2H-chromen-7-ol and (2R)-methyl 2-(4-(3-hydroxypropoxy)phenoxy)-2-methylbutanoate.

$^1$H-NMR (400 MHz, CDCl$_3$): δ 7.28 (s, 1H), 6.89 (d, 2H, J=8.2 Hz), 6.81 (d, 2H, J=9.2 Hz), 6.51 (s, 1H), 5.98 (s, 1H), 4.21 (t, 2H, J=6.0 Hz), 4.18 (t, 2H, J=6.0), 2.0-1.68 (m, 6H), 1.41 (s, 3H), 1.07(t, 3H, J=7.3 Hz), 0.95 (t, 3H, J=7.5 Hz).

Example 9

(2R)-2-(4-(3-((6-Chloro-2,2-dimethyl-4-(isopropyl)-2H-chromen-7-yl)oxy)propoxy)phenoxy)-2-methylbutanoic acid

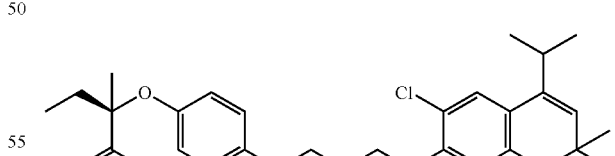

STEP A: 6-Chloro-2,2-dimethyl-4-(isopropyl)-2H-chromen-7-ol

A mixture of 4-chlororesorcinol (2.0 g, 13.84 mmol) and ethyl isobutyrylacetate (3.3 g, 20.7 mmol) in Eaton's reagent (15 mL) was stirred at ambient temperature for 16 h, poured over ice and the precipitated solids filtered, dried, and crystallized from aqueous methanol to provide the desired 6-chloro-2,2-dimethyl-4-(isopropyl)-2H-chromen-7-ol (2.68 g).

$^1$H-NMR (400 MHz, CDCl$_3$): δ 7.15 (s, 1H), 6.54 (s, 1H), 5.52 (s, 1H), 5.34 (s, 1H), 2.75 (m, 1H), 1.4 (s, 6H), 1.15 (t, 6H, J=6.9 H).

STEP B: (2R)-2-(4-(3-((6-Chloro-2,2-dimethyl-4-(isopropyl)-2H-chromen-7-yl)oxy)propoxy)phenoxy)-2-methylbutanoic acid The title compound was prepared following the procedure described in Example 1, Step F-G employing 6-chloro-2,2-dimethyl-4-(isopropyl)-2H-chromen-7-ol.

$^1$H-NMR (400 MHz, CDCl$_3$): δ 7.2 (s, 1H), 6.9 (d, 2H, J=8.9 Hz), 6.84 (d, 2H, J=8.9 Hz), 6.5 (s, 1H), 5.32 (s, 1H), 4.2-4.16 (m, 4H), 2.77 (m, 1H), 2.31(m, 2H), 2.0-1.8 (m, 2H), 1.43 (s, 3H), 1.4 (s, 6H), 1.15 (d, 6H, J=6.7 Hz), 1.07(t, 3H, J=7.3 Hz).

What is claimed is:

1. A compound having Formula I, or a pharmaceutically acceptable salt thereof, wherein

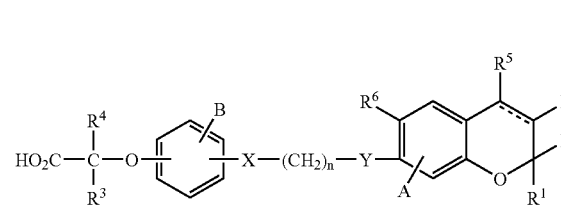

I $R^1$ and $R^2$ are each $C_1$-$C_3$ alkyl, which are optionally substituted with 1-5 halogens independently selected from F and Cl;
$R^3$ is selected from the group consisting of
  (a) H, and
  (b) $C_1$-$C_3$alkyl, which is optionally substituted with 1-5 halogens independently selected from F and Cl;
$R^4$ is $C_1$-$C_3$ alkyl, which is optionally substituted with 1-5 halogens independently selected from F and Cl;
$R^5$ is selected from the group consisting of H and $C_1$-$C_3$alkyl, which is optionally substituted with 1-5 halogens independently selected from F and Cl;
$R^6$ is selected from H, Cl, CH$_3$ and CF$_3$;
$R^7$ is selected from H and $C_1$-$C_3$ alkyl, which is optionally substituted with 1-5 halogens independently selected from F and Cl;
A and B are each selected from H, Cl, F, CH$_3$, and CF$_3$;
The dashed line connecting the ring carbon atoms attached to $R^5$ and $R^7$ is an optional double bond;
X and Y are independently selected from O and S; and
n is an integer from 2-3.

2. A compound according to claim 1, wherein X and Y are each O.

3. A compound according to claim 1, wherein A, B, and $R^7$ are H.

4. A compound according to claim 1, wherein $R^5$ is CF$_3$.

5. A compound according to claim 1, wherein $R^5$ is $C_1$-$C_3$ alkyl.

6. A compound according to claim 1, wherein $R^6$ is selected from Cl, CH$_3$ and CF$_3$.

7. A compound according to claim 6, wherein $R^6$ is Cl.

8. A compound according to claim 1, wherein $R^3$ and $R^4$ are each independently selected from CH$_3$, C$_2$H$_5$, and C$_3$H$_7$.

9. A compound according to claim 1, wherein $R^1$ and $R^2$ are each selected from CH$_3$ and C$_2$H$_5$.

10. A compound according to claim 9, wherein $R^1$ and $R^2$ are each CH$_3$.

11. A compound according to claim 1, wherein
$R^1$ and $R^2$ are each independently selected from the group consisting of CH$_3$ and C$_2$H$_5$;
R3 and R4 are each independently selected from the group consisting of CH3, C2H5, and C3H7;
$R^5$ is CF3;
$R^6$ is Cl;
$R^7$, A, and B are H;
The dashed line connecting the ring carbon atoms attached to R5 and R7 is a double bond;
X and Y are O; and
n is an integer from 2-3.

12. A compound according to claim 11, wherein $R^1$ and $R^2$ are each CH$_3$.

13. A compound according to claim 1, having the formula shown below, or a pharmaceutically acceptable salt thereof:

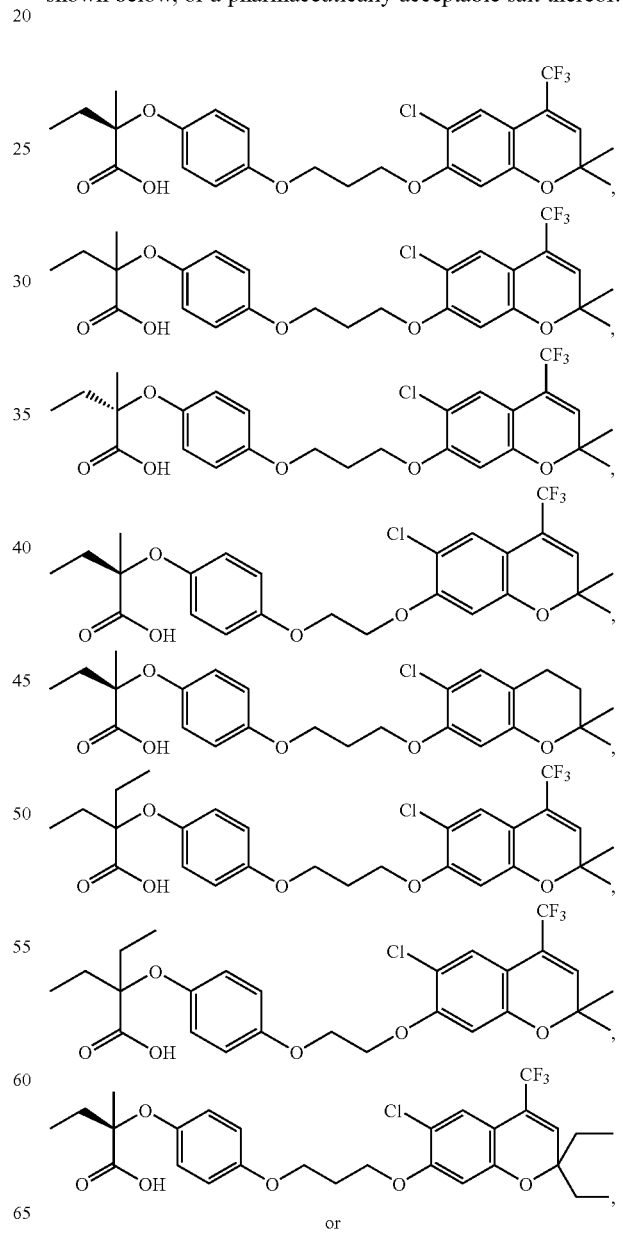

or

-continued

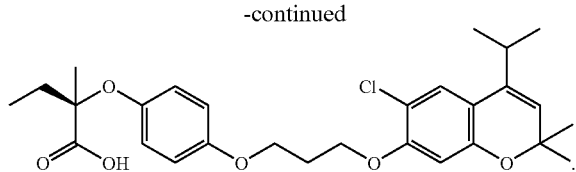

14. A pharmaceutical composition comprising a compound of claim 1, or a pharmaceutically acceptable salt thereof, and a pharmaceutically acceptable carrier.

15. A method for treating one or more lipid disorders, selected from the group consisting of dyslipidemia, hypercholesterolemia, hyperlipidemia, hypertriglyceridemia, low HDL levels, and high LDL levels in a patient in need of such treatment which comprises administering to said patient a therapeutically effective amount of a compound of claim 1.

* * * * *